(12) United States Patent
Ueda et al.

(10) Patent No.: US 10,722,154 B2
(45) Date of Patent: *Jul. 28, 2020

(54) MEDICAL PHOTOMETER AND MEDICAL PHOTOMETER CONTROL METHOD

(71) Applicant: NIHON KOHDEN CORPORATION, Shinjuku-ku, Tokyo (JP)

(72) Inventors: Yoshinori Ueda, Tokyo (JP); Teiji Ukawa, Tokyo (JP); Kazumasa Ito, Tokyo (JP); Hideki Fujisaki, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/793,303

(22) Filed: Oct. 25, 2017

(65) Prior Publication Data

US 2018/0116568 A1 May 3, 2018

(30) Foreign Application Priority Data

Oct. 27, 2016 (JP) ................................. 2016-211013

(51) Int. Cl.
*A61B 5/1455* (2006.01)
*A61B 5/145* (2006.01)
(Continued)

(52) U.S. Cl.
CPC .......... *A61B 5/1455* (2013.01); *A61B 5/1072* (2013.01); *A61B 5/1075* (2013.01);
(Continued)

(58) Field of Classification Search
CPC .... G01N 21/27; G01N 21/314; A61B 5/1455; A61B 5/14542; A61B 5/14551; A61B 5/7214
See application file for complete search history.

(56) References Cited

U.S. PATENT DOCUMENTS 5,002,391 A * 3/1991 Wolfrum ................ G01N 21/39
250/338.5
5,385,143 A * 1/1995 Aoyagi .............. A61B 5/14551
356/41

(Continued)

FOREIGN PATENT DOCUMENTS

JP 4196209 B2 12/2008

OTHER PUBLICATIONS

Communication dated Feb. 8, 2018, from the European Patent Office in counterpart European Application No. 17198546.8.

*Primary Examiner* — Violeta A Prieto
(74) *Attorney, Agent, or Firm* — Sughrue Mion, PLLC

(57) ABSTRACT

A medical photometer includes a processor and a memory that stores an instruction readable by a computer. When the instruction is executed by the processor, the medical photometer acquires a first light attenuation of a first light beam that is transmitted through or reflected from a tissue of a living body, and that has a first wavelength, based on a first intensity signal corresponding to an intensity of the first light beam, acquires a second light attenuation of a second light beam that is transmitted through or reflected from the tissue, and that has a second wavelength, based on a second intensity signal corresponding to an intensity of the second light beam, calculates a tissue thickness based on a ratio of the first light attenuation and the second light attenuation, and detects an artifact of the living body based on a temporal variation of the tissue thickness.

5 Claims, 7 Drawing Sheets

(51) Int. Cl.
*A61B 5/00* (2006.01)
*G01N 21/59* (2006.01)
*G01N 21/27* (2006.01)
*G01N 21/31* (2006.01)
*G01J 1/04* (2006.01)
*A61B 5/107* (2006.01)

(52) U.S. Cl.
CPC ........ *A61B 5/1079* (2013.01); *A61B 5/14542* (2013.01); *A61B 5/14551* (2013.01); *A61B 5/7214* (2013.01); *G01N 21/27* (2013.01); *G01N 21/59* (2013.01); *A61B 2562/0238* (2013.01); *G01J 1/04* (2013.01); *G01N 21/314* (2013.01)

(56) References Cited

U.S. PATENT DOCUMENTS

| | | | | |
|---|---|---|---|---|
| 5,490,505 A * | 2/1996 | Diab | .................. | A61B 5/14551 356/41 |
| 5,588,427 A * | 12/1996 | Tien | .................. | A61B 5/14552 356/41 |
| 5,632,272 A * | 5/1997 | Diab | .................. | G06K 9/0051 600/323 |
| 6,002,952 A * | 12/1999 | Diab | .................. | A61B 5/02416 600/310 |
| 8,560,034 B1 * | 10/2013 | Diab | .................. | G06K 9/0051 356/41 |
| 10,342,465 B2 * | 7/2019 | Ueda | .................. | A61B 5/1072 |
| 2002/0035315 A1 * | 3/2002 | Ali | .................. | A61B 5/1455 600/300 |
| 2003/0009090 A1 * | 1/2003 | Jeon | .................. | A61B 5/14535 600/323 |
| 2003/0133538 A1 * | 7/2003 | Herve | .................. | A61B 6/482 378/53 |
| 2004/0267140 A1 | 12/2004 | Ito et al. | | |
| 2005/0065415 A1 | 3/2005 | Cho et al. | | |
| 2008/0139908 A1 * | 6/2008 | Kurth | .................. | A61B 5/14553 600/340 |
| 2009/0290148 A1 * | 11/2009 | Kawanishi | .................. | G01J 1/26 356/217 |
| 2012/0232365 A1 * | 9/2012 | Ukawa | .................. | A61B 5/0261 600/324 |
| 2014/0247274 A1 | 9/2014 | Nagata | | |
| 2015/0272488 A1 * | 10/2015 | Ueda | .................. | G01N 33/4925 600/322 |
| 2017/0303788 A1 * | 10/2017 | Xavier Da Silveira | .................. | A61B 5/14552 |
| 2018/0116567 A1 * | 5/2018 | Ueda | .................. | A61B 5/1455 |
| 2018/0116569 A1 * | 5/2018 | Ueda | .................. | A61B 5/1455 |
| 2019/0083016 A1 * | 3/2019 | Ueda | .................. | A61B 5/14552 |
| 2019/0090745 A1 * | 3/2019 | Konno | .................. | A61B 5/14552 |

\* cited by examiner

MEDICAL PHOTOMETER AND MEDICAL PHOTOMETER CONTROL METHOD

CROSS REFERENCE TO RELATED APPLICATION

This application is based on Japanese Patent Applications No. 2016-211013 filed on Oct. 27, 2016, the contents of which are incorporated herein by reference.

BACKGROUND

The presently disclosed subject matter relates to a medical photometer which calculates the amount of a material having a relatively low extinction in the body of the subject, and also to a method of controlling a medical photometer for calculating the amount of the material.

A pulse photometer that is an example of a medical photometer is an apparatus which calculates the concentration of a blood light absorber of the subject as an example of photometry.

Specifically, the living tissue of the subject is irradiated with light beams at a plurality of wavelengths at which ratios of the blood extinction coefficients are different from each other depending on the blood light absorber concentration. The intensities of the light beams at the wavelengths transmitted through or reflected from the living tissue are detected. The intensities at the wavelengths are varied in accordance with the pulsation of the blood in the subject. Therefore, due to the pulsation, temporal variations of the intensities at the wavelengths are acquired in the form of a pulse wave signal. The amplitudes of pulse wave signals with respect to wavelengths correspond to light attenuation variations with respect to the same wavelengths. The blood light absorber concentration is calculated based on a ratio of light attenuation variations with respect to wavelengths (for example, see Japanese Patent No. 4,196,209).

There is a need for knowing a thickness of a tissue including water or adipose among materials existing in the body of the subject. However, these materials have an extinction which, as compared with the above-described blood light absorbers, is lower over the whole wavelength range (for example, 190 to 1,100 nm) where a general-purpose optical sensor is sensitive. In the specification, such a material is referred to as "weak light absorber in body."

It is an object of the presently disclosed subject matter to calculate the tissue thickness in body even with the principle of photometry.

On the other hand, a regular artifact of the subject may be recognized as a blood pulsation. Therefore, an accurate detection of the artifact of the subject is needed.

It is also an object of the presently disclosed subject matter to accurately detect an artifact of the living body which is one of causes of inhibition of the photometry.

SUMMARY

According to an aspect of the presently disclosed subject matter, a medical photometer includes:
a first light emitter that emits a first light beam having a first wavelength;
a second light emitter that emits a second light beam having a second wavelength;
a detector that outputs a first intensity signal corresponding to an intensity of the first light beam that is transmitted through or reflected from a tissue of a living body, and a second intensity signal corresponding to an intensity of the second light beam that is transmitted through or reflected from the tissue;
a processor; and
a memory that stores an instruction that is readable by a computer,
wherein, when the instruction is executed by the processor, the medical photometer
acquires a first light attenuation of the first light beam based on the first intensity signal,
acquires a second light attenuation of the second light beam based on the second intensity signal, and
calculates a tissue thickness based on a ratio of the first light attenuation and the second light attenuation, and
detects an artifact of the living body based on a temporal variation of the tissue thickness,
both the first light beam and the second light beam are infrared light beams or red light beams,
a ratio of a first extinction of a first light absorber at the first wavelength and a second extinction of the first light absorber at the second wavelength is different from 1,
a third extinction of a second light absorber at the first wavelength is higher than the first extinction,
a fourth extinction of the second light absorber at the second wavelength is higher than the second extinction, and
a ratio of the third extinction and the fourth extinction is approximable by 1.

According to another aspect of the presently disclosed subject matter, a medical photometer includes:
a processor; and
a memory which stores an instruction that is readable by a computer,
wherein, when the instruction is executed by the processor, the medical photometer
acquires a first light attenuation of a first light beam that has a first wavelength and that is transmitted through or reflected from a tissue of a living body, based on a first intensity signal corresponding to an intensity of the first light beam,
acquires a second light attenuation of a second light beam that has a second wavelength and that is transmitted through or reflected from the tissue of the living body, based on a second intensity signal corresponding to an intensity of the second light beam,
calculates a tissue thickness based on a ratio of the first light attenuation and the second light attenuation, and
detects an artifact of the living body based on a temporal variation of the tissue thickness,
a ratio of a first extinction of a first light absorber at the first wavelength and a second extinction of the first light absorber at the second wavelength is different from 1,
a third extinction of a second light absorber at the first wavelength is higher than the first extinction,
a fourth extinction of the second light absorber at the second wavelength is higher than the second extinction, and
a ratio of the third extinction and the fourth extinction is approximable by 1.

According to another aspect of the presently disclosed subject matter, a method of controlling a medical photometer includes:
causing the medical photometer to acquire a first light attenuation of a first light beam that has a first wavelength and that is transmitted through or reflected from a tissue of a living body, based on a first intensity signal corresponding to an intensity of the first light beam;
causing the medical photometer to acquire a second light attenuation of a second light beam that has a second wavelength and that is transmitted through or reflected from the tissue, based on a second intensity signal corresponding to an intensity of the second light beam;

causing the medical photometer to calculate a tissue thickness based on a ratio of the first light attenuation and the second light attenuation; and causing the medical photometer to detect an artifact of the living body based on a temporal variation of the tissue thickness, wherein a ratio of a first extinction of the first light absorber at the first wavelength and a second extinction of the first light absorber at the second wavelength is different from 1, a third extinction of a second light absorber at the first wavelength is higher than the first extinction, a fourth extinction of the second light absorber at the second wavelength is higher than the second extinction, and a ratio of the third extinction and the fourth extinction is approximable by 1.

According to the above-described modes, while using the principle of photometry, the tissue thickness in body can be calculated. Further, an artifact of the living body which is one of causes of inhibition of the photometry can be correctly detected.

DETAILED DESCRIPTION OF EMBODIMENTS

Figure 1:
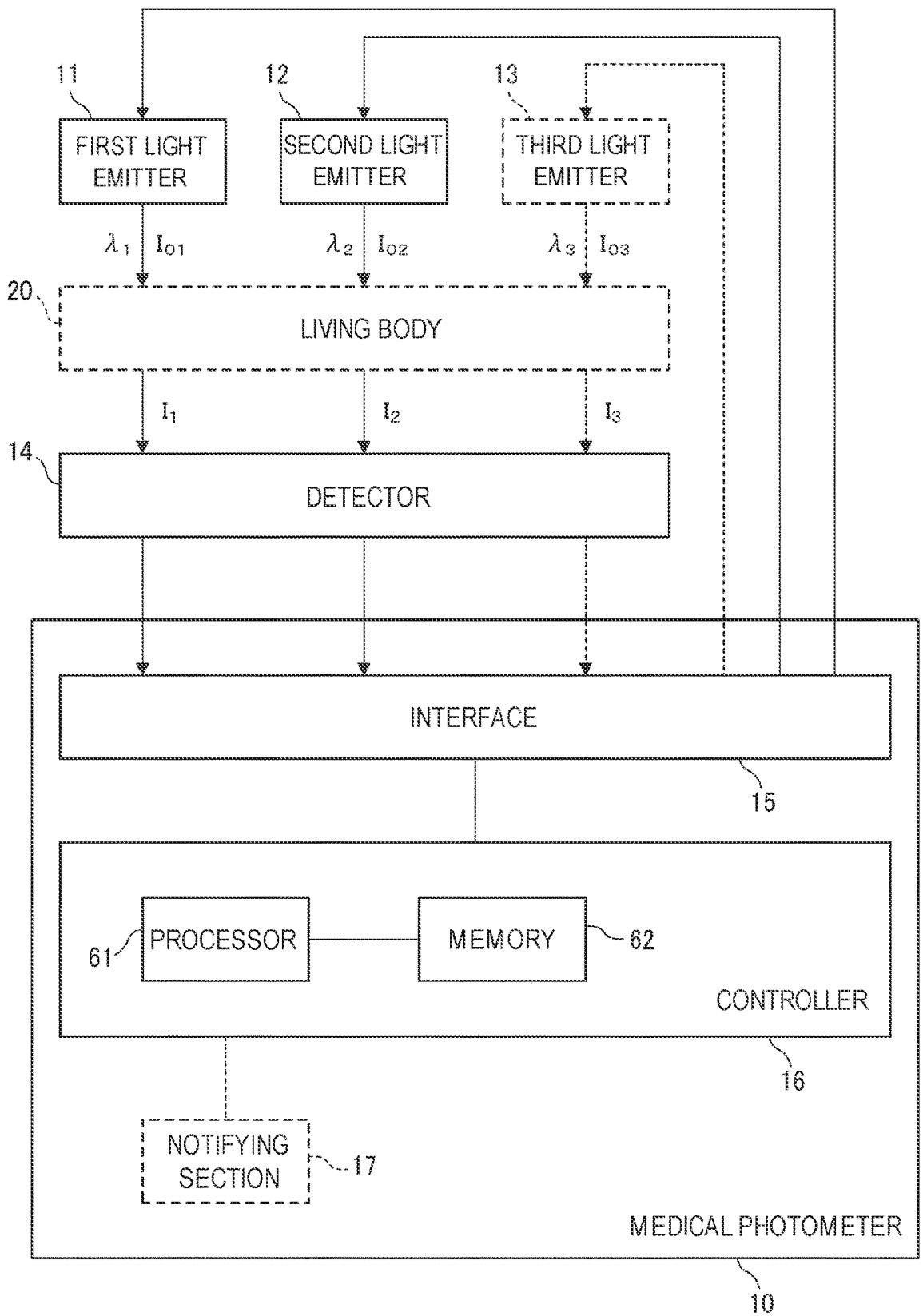
FIG. 1 is a diagram illustrating the functional configuration of a medical photometer of a first embodiment.

Hereinafter, embodiments will be described in detail with reference to the accompanying drawings. FIG. 1 is a diagram illustrating the functional configuration of a medical photometer 10 of a first embodiment. The medical photometer 10 is an apparatus which calculates the amount of a weak light absorber in the living body 20.

The medical photometer 10 may include a first light emitter 11, a second light emitter 12, a detector 14, an interface 15, and a controller 16.

The first light emitter 11 is configured so as to emit a first light beam having a first wavelength $\lambda_1$. The second light emitter 12 is configured so as to emit a second light beam having a second wavelength $\lambda_2$. An example of the first wavelength $\lambda_1$ is 880 nm. An example of the second wavelength $\lambda_2$ is 940 nm. Namely, both the first and second light beams are infrared light beams.

For example, the first light emitter 11 is a semiconductor light emitting device which can emit the first light beam. For example, the second light emitter 12 is a semiconductor light emitting device which can emit the second light beam. Examples of such a semiconductor light emitting device are a light emitting diode (LED), a laser diode, and an organic electroluminescence element.

As shown in FIG. 1, the detector 14 is configured so as to output a first intensity signal in accordance with the intensity $I_1$ of the first light beam that is transmitted through or reflected from a tissue of a living body 20 (the finger or ear lobe of the subject). The detector 14 is further configured so as to output a second intensity signal in accordance with the intensity $I_2$ of the second light beam that is transmitted through or reflected from the living body 20. For example, the detector 14 is an optical sensor having a sensitivity to the first wavelength $\lambda_1$ and the second wavelength $\lambda_2$. Examples of the optical sensor are a photodiode, a phototransistor, and a photoresistor.

The first light emitter 11, the second light emitter 12, and the detector 14 are connected to the interface 15. The interface 15 is a connector which allows signals to pass therethrough. The connection may be realized as wired or wireless connection.

The controller 16 is communicably connected to the first light emitter 11, the second light emitter 12, and the detector 14 through the interface 15. Therefore, the controller 16 can control the operations of the first light emitter 11 and the second light emitter 12 through the interface 15. The controller 16 can receive the first and second intensity signals from the detector 14 through the interface 15.

The controller 16 may include a processor 61 and a memory 62.

Examples of the processor 61 are a CPU and an MPU. The memory 62 is configured so as to store an instruction that is readable by a computer. Examples of the memory 62 are a ROM which stores various instructions, and a RAM having a work area in which various instructions are executed by the processor 61.

Figure 2:
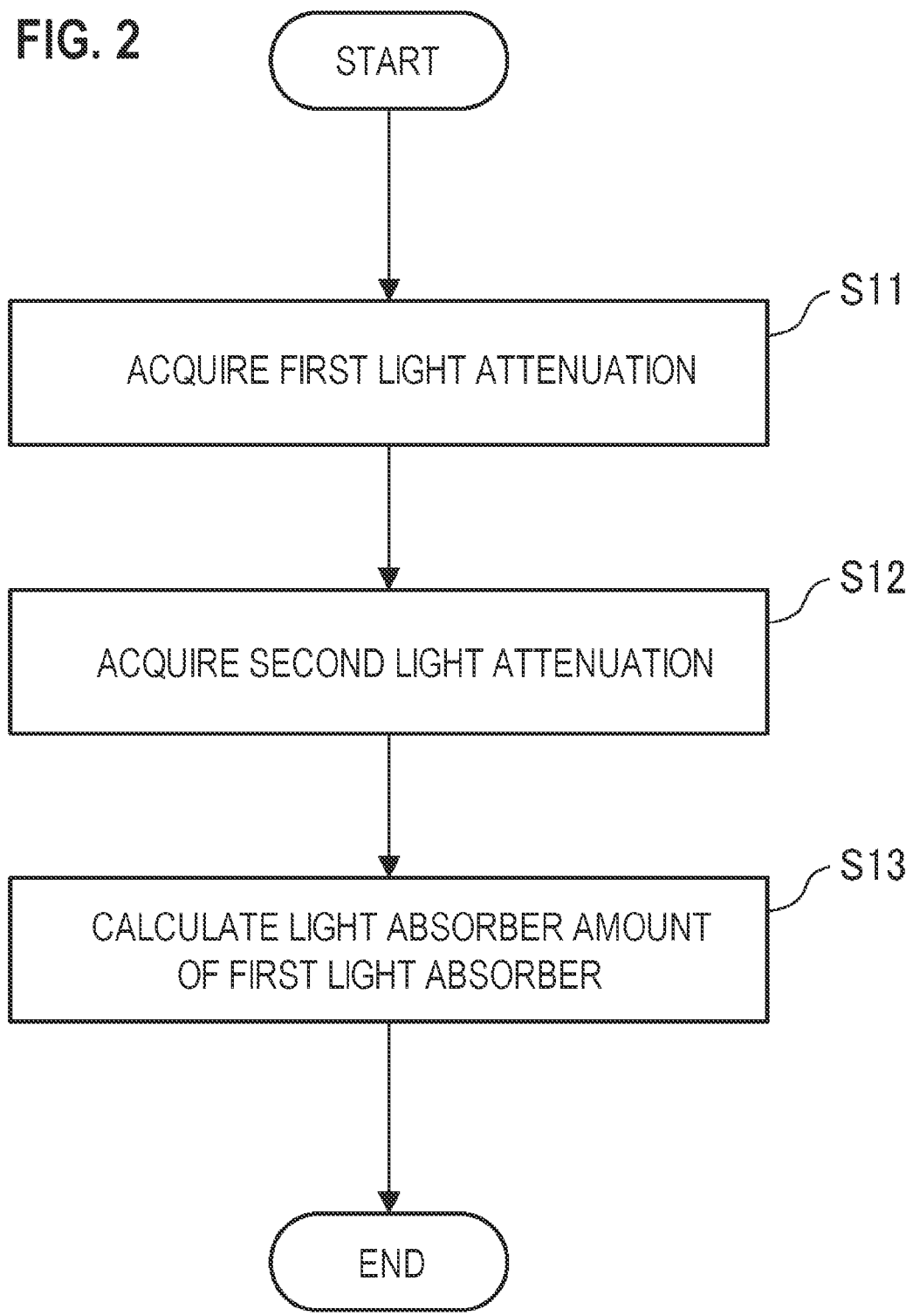
FIG. 2 is a flowchart illustrating the operation of the medical photometer in FIG. 1.

The medical photometer 10 is configured so as to execute the process shown in FIG. 2 when an instruction stored in the memory 62 is executed by the processor 61.

A light attenuation (first light attenuation) $A_1$ of the first light beam that is transmitted through or reflected from the living body 20 is acquired based on the first intensity signal supplied from the detector 14 (step S11).

The first light emitter 11 is controlled by the controller 16, and therefore the controller 16 already knows the intensity $I_{O1}$ of the first light beam emitted from the first light emitter 11. Based on the intensity $I_1$ of the first light beam which is detected by the detector 14, therefore, the first light attenuation $A_1$ is acquired by the following expression:

$$A_1 ln(I_{O1}/I_1) \tag{1}$$

Next, a light attenuation (second light attenuation) $A_2$ of the second light beam that is transmitted through or reflected from the living body 20 is acquired based on the second intensity signal supplied from the detector 14 (step S12).

The second light emitter 12 is controlled by the controller 16, and therefore the controller 16 already knows the intensity $I_{O2}$ of the second light beam emitted from the second light emitter 12. Based on the intensity $I_2$ of the second light beam which is detected by the detector 14, therefore, the second light attenuation $A_2$ is acquired by the following expression:

$$A_2 = ln(I_{O2}/I_2) \tag{2}$$

Steps S11 and S12 may be performed in parallel, or step S12 may be performed in advance of step S11.

Then, the amount of the weak light absorber in the tissue of the living body 20 which the first and second light beams are transmitted through or reflected from is calculated based on the first and second light attenuations $A_1$ and $A_2$ which are acquired as described above (step S13).

Figure 3:
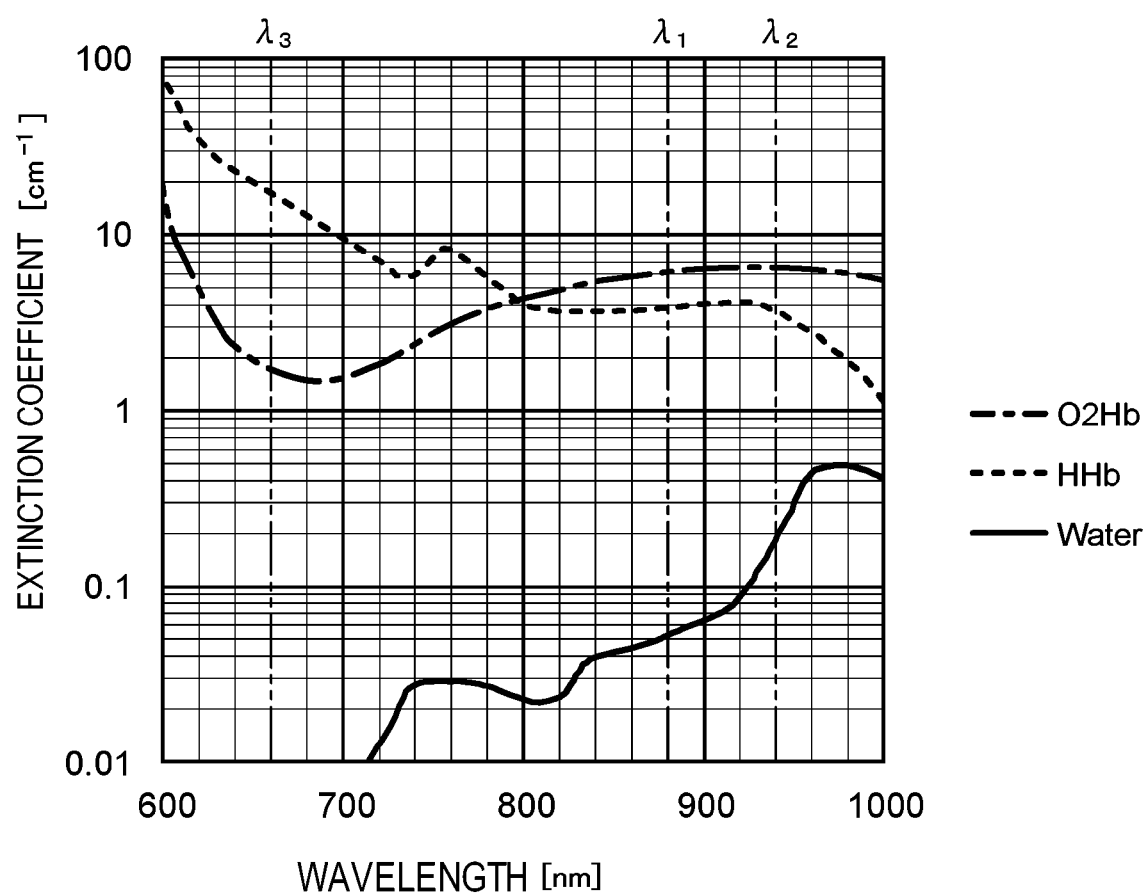
FIG. 3 is illustrates the operation of the medical photometer in FIG. 1.

In FIG. 3, the solid line indicates the extinction spectrum of water (an example of the first light absorber), the broken line indicates the extinction spectrum of deoxyhemoglobin, and the dash-dot line indicates the extinction spectrum of oxyhemoglobin (an example of the second light absorber).

As seen from the figure, the extinction (an example of the first extinction) of water at the first wavelength $\lambda_1$ of the first light beam, and the extinction (an example of the second extinction) of water at the second wavelength $\lambda_2$ of the second light beam are different from each other. In other words, a ratio of the extinction of water at the first wavelength $\lambda_1$ and that of water at the second wavelength $\lambda_2$ is different from 1. In the specification, the term "different from 1" means that the ratio has a value of 2 or larger, or 0.5 or smaller.

The extinction (an example of the third extinction) of hemoglobin at the first wavelength $\lambda_1$ of the first light beam is higher than that of water at the same wavelength. Similarly, the extinction (an example of the fourth extinction) of hemoglobin at the second wavelength $\lambda_2$ of the second light beam is higher than that of water at the same wavelength. In other words, the extinction of water is lower than that of hemoglobin at the first and second wavelengths $\lambda_1$ and $\lambda_2$. Namely, water is an example of the weak light absorber in body.

On the other hand, the extinction of hemoglobin at the first wavelength $\lambda_1$ and that of hemoglobin at the second wavelength $\lambda_2$ are substantially equal to each other. In other words, a ratio of the extinction of hemoglobin at the first wavelength $\lambda_1$ and that of hemoglobin at the second wavelength $\lambda_2$ can be approximated by 1. In the specification, the term "can be approximated by 1" means that the ratio has a value smaller than 2 or larger than 0.5.

In the embodiment, namely, the first and second wavelengths $\lambda_1$ and $\lambda_2$ are selected so that a weak light absorber in body (the first light absorber) the amount of which is to be specified has substantially different extinctions at $\lambda_1$ and $\lambda_2$, and that a light absorber (the second light absorber) which is higher in extinction than the weak light absorber in body shows substantially equal extinctions at $\lambda_1$ and $\lambda_2$.

The above-described first light attenuation $A_1$ is the sum of the contribution of the light attenuation due to the first light absorber at the first wavelength $\lambda_1$, and that of the light attenuation due to the second light absorber, and can be indicated by the following expression:

$$A_1 = E_{11} C_1 D_1 + E_{21} C_2 D_2 \quad (3)$$

where $E_{11}$ indicates the extinction coefficient ($M^{-1}$ cm$^{-1}$) of the first light absorber at the first wavelength $\lambda_1$, $C_1$ indicates the concentration (M) of the first light absorber, $D_1$ indicates the optical path length (cm) of a portion where extinction is performed by the first light absorber, $E_{21}$ indicates the extinction coefficient ($M^{-1}$ cm$^{-1}$) of the second light absorber at the first wavelength $\lambda_1$, $C_2$ indicates the concentration (M) of the second light absorber, and $D_2$ indicates the optical path length (cm) of a portion where extinction is performed by the second light absorber.

Same or similarly, the above-described second light attenuation $A_2$ is the sum of the contribution of the light attenuation due to the first light absorber at the second wavelength $\lambda_2$, and that of contribution of the light attenuation due to the second light absorber, and can be indicated by the following expression:

$$A_2 = E_{12} C_1 D_1 + E_{22} C_2 D_2 \quad (4)$$

where $E_{12}$ indicates the extinction coefficient ($M^{-1}$ cm$^{-1}$) of the first light absorber at the second wavelength $\lambda_2$, and $E_{22}$ indicates the extinction coefficient ($M^{-1}$ cm$^{-1}$) of the second light absorber at the second wavelength $\lambda_2$.

As described above, the contribution of the light attenuation due to the second light absorber at the first wavelength $\lambda_1$, and that of the light attenuation due to the second light absorber at the second wavelength $\lambda_2$ are substantially equal to each other. When the difference between the first light attenuation $A_1$ and the second light attenuation $A_2$ is obtained, therefore, the contribution of the light attenuation due to the second light absorber can be neglected, and only the contribution of the light attenuation due to the first light absorber can be extracted.

This fact is indicated with Expressions (1) to (4) as follows:

$$A_1 - A_2 = (E_{11} C_1 D_1 + E_{21} C_2 D_2) - (E_{12} C_1 D_1 + E_{22} C_2 D_2)$$

$$ln(I_{O1}/I_1) - ln(I_{O2}/I_2) \cong (E_{11} - E_{12}) C_1 D_1$$

$$ln(I_2/I_1) - ln(I_{O2}/I_{O1}) \cong (E_{11} - E_{12}) C_1 D_1 \quad (5)$$

In Expression (5), the second term of the left side is a ratio of the intensity of the first light beam emitted from the first light emitter 11, and that of the second light beam emitted from the second light emitter 12. As described above, these values are already known, and therefore the second term of the left side can be treated as a constant. On the other hand, also $E_{11}$ and $E_{12}$ in the right side are constants. Therefore, $C_1 D_1$ can be specified from a ratio of the detected intensity of the first light beam by the detector 14, and that of the second light beam. This value corresponds to the amount of the first light absorber, i.e., the weak light absorber in body.

According to the technique of the embodiment, that is, the amount of the weak light absorber in body can be calculated even with the principle of photometry.

When a blood light absorber such as hemoglobin is selected as the second light absorber in the same manner as the embodiment, the first light attenuation $A_1$ can be indicated more specifically by following expression as the sum of the contribution of the light attenuation due to the arterial blood at the first wavelength $\lambda_1$, that of the light attenuation due to the venous blood, and that of the light attenuation due to tissues other than the blood:

$$A_1 = E_{a1} Hb D_a + E_{v1} Hb D_v + \Sigma E_{t1} D_t \quad (6)$$

where $E_{a1}$ indicates the extinction coefficient (dl g$^{-1}$ cm$^{-1}$) of hemoglobin in arterial blood at the first wavelength $\lambda_1$, Hb indicates the hemoglobin concentration in blood (dl g$^{-1}$), $D_a$ indicates the thickness (cm) of the blood vessel through which the arterial blood flows, $E_{v1}$ indicates the extinction coefficient (dl g$^{-1}$ cm$^{-1}$) of hemoglobin in venous blood at the first wavelength $\lambda_1$, $D_v$ indicates the thickness (cm) of the blood vessel through which the venous blood flows, $\Sigma_{t1}$ indicates the light attenuation rate (cm$^{-1}$) due to tissues other than the blood at the first wavelength $\lambda_1$, and $D_t$ indicates the thickness (cm) of tissues other than the blood, i.e., the tissue thickness.

Same or similarly, the second light attenuation $A_2$ can be indicated by the following expression as the sum of the contribution of the light attenuation due to the arterial blood at the second wavelength $\lambda_2$, that of the light attenuation due to the venous blood, and that of contribution of the light attenuation due to tissues other than the blood, and can be indicated by the following expression:

$$A_2 = E_{a2} Hb D_a + E_{v2} Hb D_v + \Sigma_{t2} D_t \quad (7)$$

where $E_{a2}$ indicates the extinction coefficient (dl g$^{-1}$ cm$^{-1}$) of hemoglobin in arterial blood at the second wavelength $\lambda_2$, $E_{v2}$ indicates the extinction coefficient (dl g$^{-1}$ cm$^{-1}$) of hemoglobin in venous blood at the second wavelength $\lambda_2$, and $\Sigma_{t2}$ indicates the light attenuation rate (cm$^{-1}$) due to tissues other than the blood at the second wavelength $\lambda_2$.

As described above, the contribution of the light attenuation due to hemoglobin at the first wavelength $\lambda_1$, and that of the light attenuation due to hemoglobin at the second wavelength $\lambda_2$ are substantially equal to each other. When the difference between the first light attenuation $A_1$ and the second light attenuation $A_2$ is obtained, therefore, the contribution of the light attenuation due to hemoglobin can be neglected, and only the contribution of the light attenuation due to the tissue thickness $D_t$ can be extracted.

This fact is indicated with Expressions (1), (2), (6), and (7) as follows:

$$A_1-A_2=(E_{a1}HbD_a+E_{v1}HbD_v+\Sigma_{t1}D_t)-(E_{a2}HbD_a+E_{v2}HbD_v+\Sigma_{t2}D_t)$$

$$ln(I_{O1}/I_1)-ln(I_{O2}/I_2)\cong(\Sigma_{t1}-\Sigma_{t2})D_t$$

$$ln(I_2/I_1)-ln(I_{O2}/I_{O1})\cong(\Sigma_{t1}-\Sigma_{t2})D_t \quad (8)$$

In Expression (8), the second term of the left side is a ratio of the intensity of the first light beam emitted from the first light emitter 11, and that of the second light beam emitted from the second light emitter 12. As described above, these values are already known, and therefore the second term of the left side can be treated as a constant. On the other hand, also $\Sigma_{t1}$ and $\Sigma_{t2}$ in the right side are constants. Therefore, the tissue thickness $D_t$ can be specified from a ratio of the detected intensity of the first light beam by the detector 14, and that of the second light beam.

As an index indicating the degree of the blood circulation, the perfusion index is known. Even when the blood vessel pulsates at the same expansion rate, different perfusion indices may be acquired with photometry depending on the difference in tissue thickness. In the case of a subject having large fingers (the tissue thickness is large), the perfusion index generally tends to have a large value. In other words, when attention is focused only on the fact that the value of the perfusion index is small, it is not possible to accurately distinguish whether the fact is caused by insufficient perfusion of blood or by a small tissue thickness.

According to the configuration of the embodiment, the tissue thickness of the living body 20 can be specified with the principle of photometry, and therefore it is possible to provide information which can compensate insufficient information named the perfusion index. Consequently, the degree of the blood circulation in the living body 20 can be determined more accurately As indicated by the broken line in FIG. 1, the medical photometer 10 may include a third light emitter 13. The third light emitter 13 is configured so as to emit a third light beam having a third wavelength $\lambda_3$. As shown in FIG. 3, an example of the third wavelength $\lambda_3$ is 660 nm. For example, the third light emitter 13 is a semiconductor light emitting device which can emit the third light beam. Examples of such a semiconductor light emitting device are a light emitting diode (LED), a laser diode, and an organic electroluminescence element.

The third wavelength $\lambda_3$ is selected as a wavelength which satisfies the following conditions.

The ratio of the extinction coefficient of the blood at the first wavelength $\lambda_1$, and that of the blood at the third wavelength $\lambda_3$ is varied in accordance with the concentration of the target light absorber (in the example, oxyhemoglobin) contained in the blood.

The ratio of the extinction coefficient of the blood at the second wavelength $\lambda_2$, and that of the blood at the third wavelength $\lambda_3$ is varied in accordance with the concentration of the target light absorber (in the example, oxyhemoglobin) contained in the blood.

In this case, the detector 14 is configured so as to output a third intensity signal in accordance with the intensity $I_3$ of the third light beam that is transmitted through or reflected from the tissue of the living body 20.

In this case, the third light emitter 13 is connected to the interface 15. The connection may be realized as wired or wireless connection.

In this case, the controller 16 is communicably connected to the third light emitter 13 through the interface 15. Therefore, the controller 16 can control the operation of the third light emitter 13 through the interface 15. The controller 16 can receive the third intensity signal from the detector 14 through the interface 15.

In this case, when an instruction stored in the memory 62 is executed by the processor 61, the medical photometer 10 acquires a light attenuation variation $\Delta A_3$ of the third light beam due to the blood pulsation in the tissue (the place where the first and second light attenuations $A_1$ and $A_2$ are acquired) of the living body 20 based on the third intensity signal and at least one of the first and second intensity signals supplied from the detector 14. Then, a ratio of oxyhemoglobin to the amount of hemoglobin capable of carrying oxygen in the arterial blood, i.e., the arterial oxygen saturation (an example of the concentration of the second light absorber) is calculated based on the light attenuation variation $\lambda A_3$ of the third light beam and at least one of the acquired light attenuation variations $\lambda A_1$ and $\lambda A_2$ of the first and second light beams. The technique for calculating the arterial oxygen saturation with the principle of pulse photometry is well known, and therefore its detailed description is omitted.

According to the configuration, with the third light beam and at least one of the first and second light beams, the arterial oxygen saturation can be calculated with the principle of so-called pulse photometry. That is, the above-described configuration for specifying the amount of the weak light absorber in body can be integrated into a conventional probe which is to be used in pulse photometry. Namely, the user is allowed to easily calculate the amount of the weak light absorber in body and the arterial oxygen saturation, by simply attaching the probe to the tissue of the living body 20.

Figure 4:
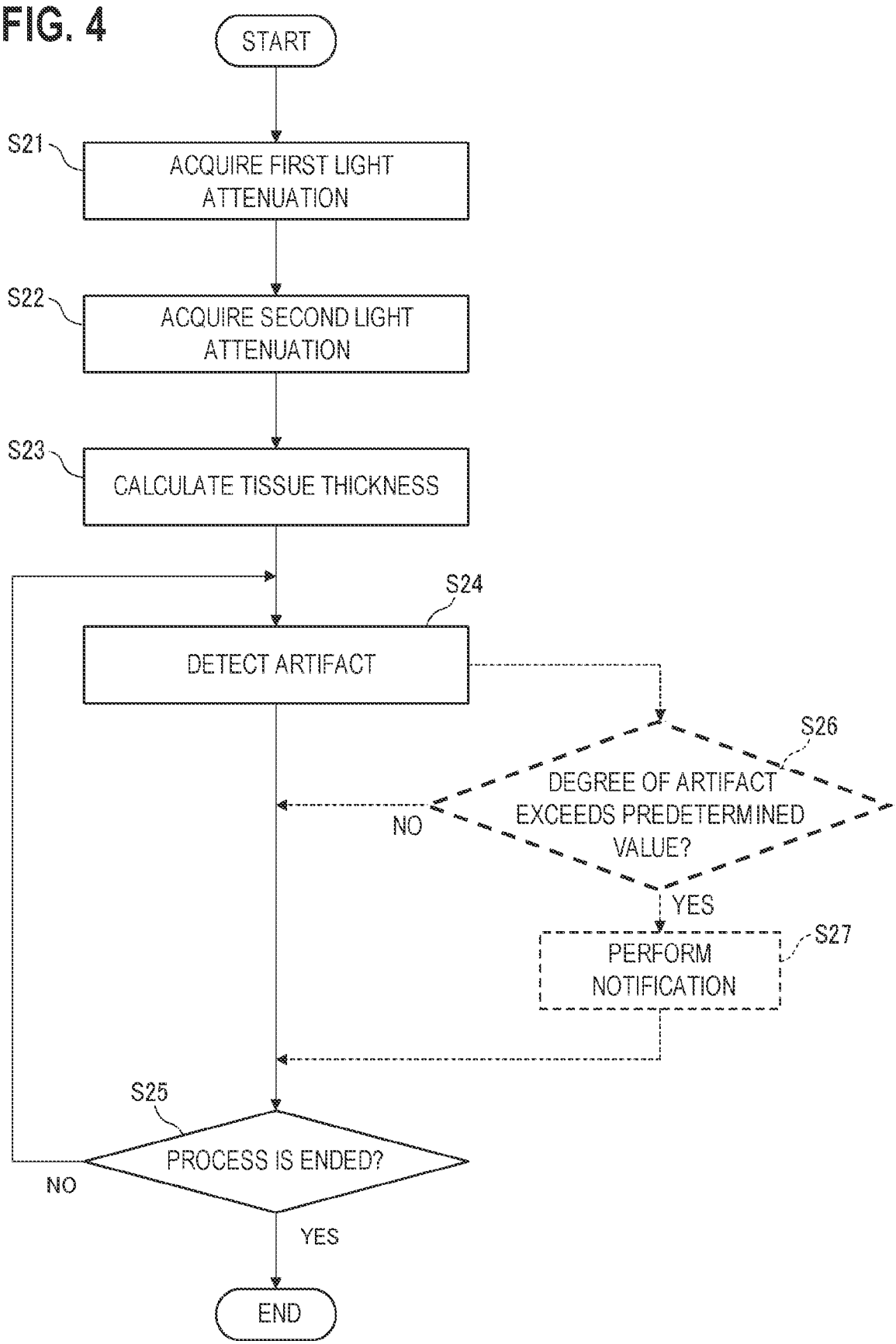
FIG. 4 is a flowchart illustrating the operation of a medical photometer of a second embodiment.

Referring to FIG. 4, next, a second embodiment of the process which can be executed by the medical photometer 10 having the configuration shown in FIG. 1 will be described.

Similarly with step S11 shown in FIG. 2, the first light attenuation $A_1$ due to transmission through or reflection from the living body 20 is acquired based on the first intensity signal supplied from the detector 14 (step S21).

Similarly with step S12 shown in FIG. 2, next, the second light attenuation $A_2$ due to transmission through or reflection from the living body 20 is acquired based on the second intensity signal supplied from the detector 14 (step S22).

Steps S21 and S22 may be performed in parallel, or step S22 may be performed in advance of step S21.

Then, the tissue thickness $D_t$ of the living body 20 which the first and second light beams are transmitted through or reflected from is calculated based on the first and second light attenuations $A_1$ and $A_2$ that are acquired as described above (step S23). The calculation of the tissue thickness $D_t$ is performed with Expressions (6) to (8) which have been described with reference to step S13 in FIG. 2.

Then, an artifact of the living body 20 is detected based on a variation $\Delta D_t$ of the tissue thickness $D_t$ which is calculated in step S23 (step S24).

The tissue thickness $D_t$ of the interested living body 20 is varied by an artifact of the living body 20. In the case where the tissue thickness is varied from $D_t$ to $(D_t+\Delta D_t)$ Expression (8) for obtaining the tissue thickness $D_t$ can be transformed into the following manner. Here, the value $(I_2/I_1)$ in Expression (8), i.e., the intensity ratio of the first and second light beams detected by the detector 14 is expressed as R, and the value $(I_{02}/I_{01})$ in Expression (8), i.e., the intensity ratio of the light beams emitted from the first and second light emitters 11 and 12 is expressed as $R_O$. In this case, it is assumed that the value of the intensity ratio R is varied to $(R+\Delta R)$ by an artifact of the living body 20.

$$ln(R)-ln(R_O) \cong (\Sigma_{t1}-\Sigma_{t2})D_t$$

$$ln(R+\Delta R)-ln(R_O) \cong (\Sigma_{t1}-\Sigma_{t2})(D_t+\Delta D_t)$$

$$ln(R+\Delta R)-ln(R) \cong (\Sigma_{t1}-\Sigma_{t2})(D_t+\Delta D_t)-(\Sigma_{t1}-\Sigma_{t2})D_t$$

$$ln[(R+\Delta R)/R] \cong (\Sigma_{t1}-\Sigma_{t2})\Delta D_t$$

When it is assumed that $\Delta R$ is sufficiently smaller than R, the following expression is obtained:

$$\Delta R/R \cong (\Sigma_{t1}-\Sigma_{t2})\Delta D_t \qquad (9)$$

It is seen that the variation rate $(\Delta R/R)$ of the intensity ratio is proportional to the variation $\Delta D_t$ of the tissue thickness.

That is, the controller 16 monitors the temporal variation of the tissue thickness $D_t$ by observing the temporal variation of the intensity ratio R of the first and second light beams detected by the detector 14. When a variation $\Delta R$ occurs in the intensity ratio R, it can be deemed that $\Delta D_t$ is caused also in the tissue thickness $D_t$.

Figure 6:
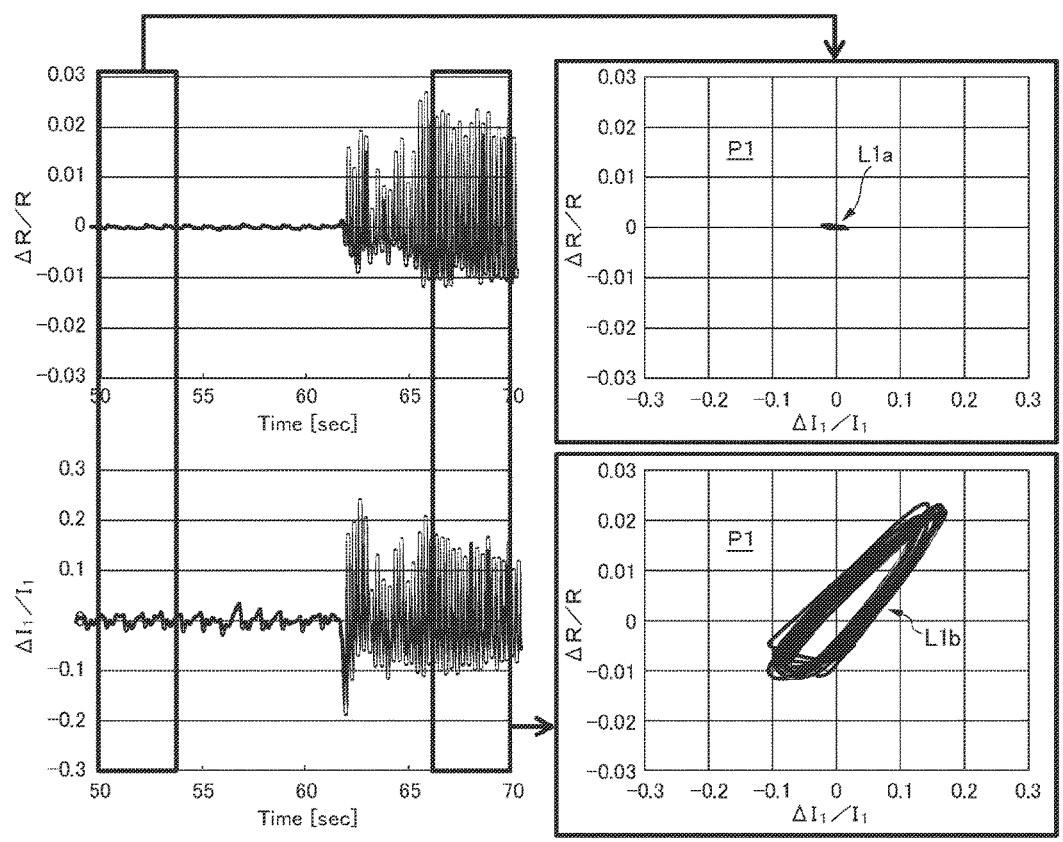
FIG. 6 illustrates the operations of the medical photometers in FIGS. 4 and 5.

The lower left graph in FIG. 6 illustrates a temporal variation of the intensity $I_1$ of the first light beam detected by the detector 14. The left half of the graph illustrates a rest state, and the right half illustrates a state where a large artifact is intentionally induced. It is seen that the intensity I1 is periodically varied also in the rest state. The periodic variation is due to pulsation of the living body 20.

Although an extremely large artifact is indicated in the graph, there is a case where a variation of the detected intensity due to a relatively small artifact (particularly by a regular artifact) is hardly distinguished from that due to pulsation by simply monitoring the detected intensity of the first or second light beam.

By contrast, the upper left graph in FIG. 6 illustrates a temporal variation of the intensity ratio R of the first and second light beams detected by the detector 14. The left half of the graph illustrates a rest state, and the right half illustrates a state where a large artifact is intentionally induced. As compared with the lower left graph, it is seen that the periodic variation of the intensity ratio due to pulsation is suppressed in the rest state.

Namely, having the detector 14 detect a temporal variation of the intensity ratio R of the first and second light beams which corresponds to a temporal variation of the tissue thickness Dt, a variation of the detected intensity due to pulsation can be cancelled out, and a variation of the detected intensity due to an artifact can be more clearly extracted. This is because pulsation does not have a substantial influence on the tissue thickness $D_t$.

According to the configuration of the embodiment, therefore, the tissue thickness of a living body can be calculated with the principle of photometry, and moreover an artifact of the living body which is one of factors affecting the photometry can be accurately detected.

When the process of detecting an artifact is ended, it is determined whether the whole process is to be ended or not (step S25). If it is determined that the whole process is to be ended (YES in step S25), the whole process is ended. If it is determined that the whole process is not to be ended (NO in step S25), the process of detecting an artifact (step S24) is repeated.

As indicated by the broken line in FIG. 1, the medical photometer 10 of the embodiment may include a notifying section 17. The notifying section 17 is configured so as to perform notification when the degree of the detected artifact exceeds a predetermined value. The notification is performed by at least one of visual notification and auditory notification.

Specifically, the medical photometer 10 is configured so as to perform the processes indicated by the broken line in FIG. 4 when an instruction stored in the memory 62 is executed by the processor 61.

When an artifact is detected in step S24, it is determined whether the degree of the artifact exceeds the predetermined value or not (step S26). The predetermined value is adequately adjustable by the user. Specifically, it is determined whether the variation rate of the intensity ratio R which is indicated in the upper left graph in FIG. 6 exceeds the predetermined value or not. A situation where the conditions are continued to be satisfied for a predetermined period of time may be added to criteria for the determination.

If it is determined that the degree of the detected artifact exceeds the predetermined value (YES in step S26), the notification is performed (step S27). As described above, the notification can be performed by at least one of visual notification and auditory notification. After the notification, the process is transferred to step S25, and the above-described processes are repeated.

If it is determined that the degree of the detected artifact is equal to or smaller than the predetermined value (NO in step S26), the process is transferred to step S25, and the above-described processes are repeated.

According to the configuration, the user is notified of an artifact of the living body 20 which may disturb the operation of the medical photometer 10, and thereby the user can take adequate procedures. When the predetermined value is properly set, it is possible to notify of only a situation where procedures must be truly taken. This can prevent the working efficiency of the user from being lowered.

As described in the first embodiment, the first light emitter 11, the second light emitter 12, and the detector 14 can be integrated into a conventional pulse photometry probe including the third light emitter 13.

In conventional pulse photometry, in order to avoid a situation where an artifact has an adverse influence on a calculated result of the arterial oxygen saturation, an independent sensor (such as an acceleration sensor) for detecting an artifact must be attached to the living body. In the embodiment, by contrast, a configuration for calculating the tissue thickness can be integrated into a probe for calculating the arterial oxygen saturation, and moreover an artifact can be detected with the probe. Therefore, a situation where an artifact has an adverse influence on a calculated result of the arterial oxygen saturation can be avoided without adding an independent sensor.

Figure 5:
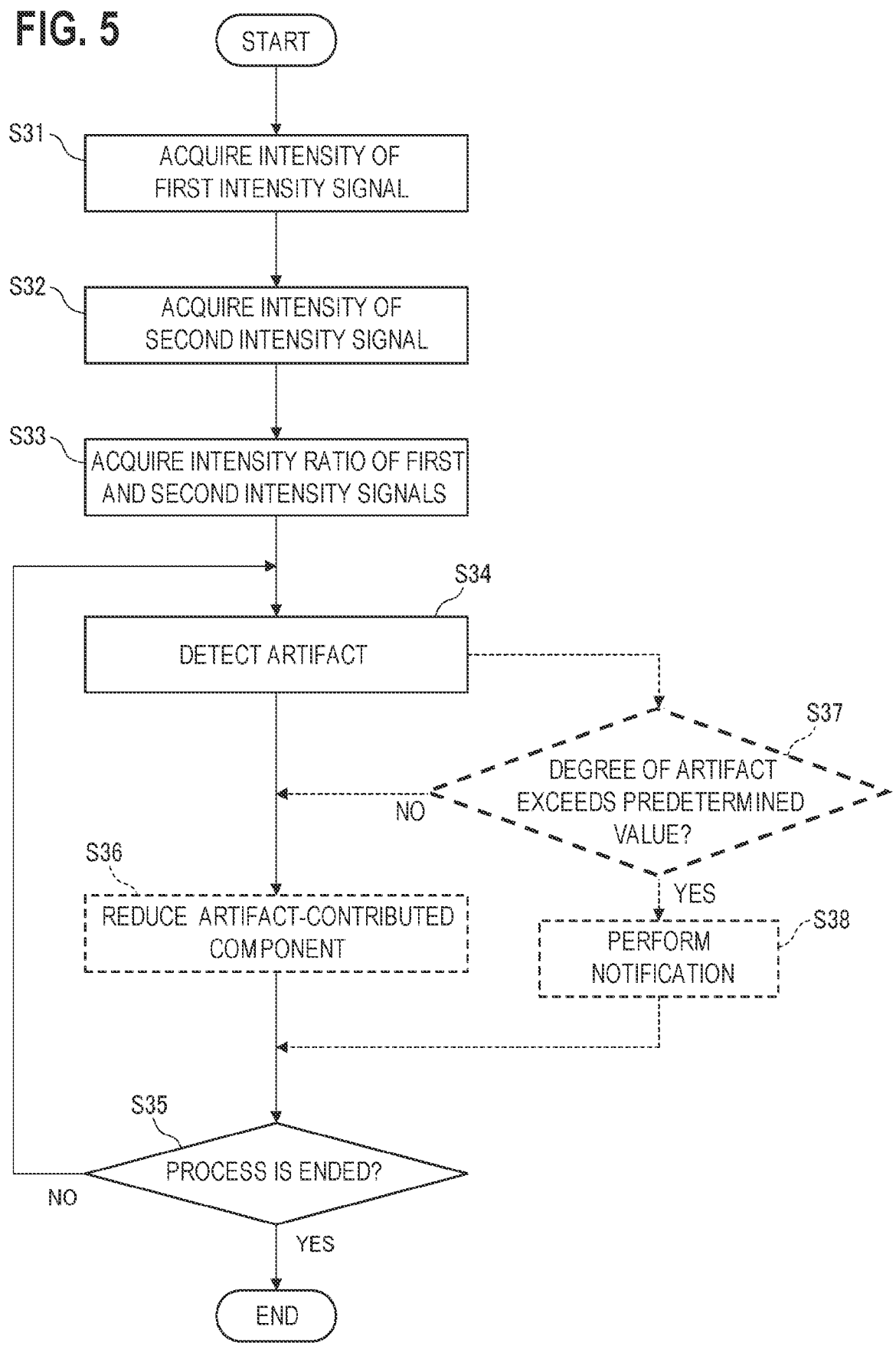
FIG. 5 is a flowchart illustrating the operation of a medical photometer of a third embodiment.

Referring to FIG. 5, next, a third embodiment of the process which can be executed by the medical photometer 10 having the configuration shown in FIG. 1 will be described.

The intensity of the first intensity signal corresponding to the intensity $I_1$ of the first light beam which is emitted from the first light emitter 11 and detected by the detector 14 is acquired (step S31).

Next, the intensity of the second intensity signal corresponding to the intensity $I_2$ of the second light beam which is emitted from the second light emitter 12 and detected by the detector 14 is acquired (step S32).

Steps S31 and S32 may be performed in parallel, or step S32 may be performed in advance of step S31.

Then, an intensity ratio which is a ratio of the intensity of the first intensity signal acquired in step S31, and that of the second intensity signal acquired in step S32 is obtained (step S33). The intensity ratio has a value corresponding to the intensity ratio R ($=I_2/I_1$) which has been described in the second embodiment.

When the temporal variation of the intensity ratio of the first and second intensity signals is monitored, therefore, an artifact of the living body 20 can be detected (step S34). At this time, the first wavelength $\lambda_1$ and the second wavelength $\lambda_2$ must be selected so as to enable the tissue thickness $D_t$ to be calculated. However, the calculation of the tissue thickness $D_t$ which has been described in the second embodiment is not essential.

According to the configuration, an artifact of the living body which is one of factors affecting the photometry can be accurately detected even with the principle of photometry.

When the process of detecting an artifact is ended, it is determined whether the whole process is to be ended or not (step S35). If it is determined that the whole process is to be ended (YES in step S35), the whole process is ended. If it is determined that the whole process is not to be ended (NO in step S35), the process of detecting an artifact (step S34) is repeated.

As an example of a technique for detecting an artifact, a coordinate plane P1 shown in the right half in FIG. 6 is used. The abscissa of the coordinate plane P1 indicates the variation rate of the intensity of the first or second intensity signal. Namely, the abscissa of the coordinate plane P1 corresponds to the variation rate of the intensity $I_1$ of the first light beam detected by the detector 14, or that of the intensity $I_2$ of the second light beam (in the illustrated example, the abscissa corresponds to the variation rate of the intensity $I_1$ of the first light beam). The ordinate of the coordinate plane P1 indicates the variation rate of the intensity ratio of the first and second intensity signals. Namely, the ordinate of the coordinate plane P1 corresponds to the variation rate of the intensity ratio R of the first and second light beams detected by the detector 14.

In the embodiment, an artifact of the living body 20 can be detected based on a temporal variation of a point in the coordinate plane P1, i.e., the shape of a locus (Lissajous figure) drawn by the point.

The upper right graph in FIG. 6 illustrates a Lissajous figure L1$a$ in the rest state. Since there is no artifact, the Lissajous figure L1$a$ does not have a substantial width in the direction of the ordinate. Only the temporal variation of the first intensity signal due to pulsation is reflected in the Lissajous figure L1$a$, and the figure has a substantial width in only the direction along the abscissa.

The lower right graph in FIG. 6 illustrates a Lissajous figure L1$b$ in the state where a large artifact is intentionally induced. In accordance with the artifact, the intensity ratio R of the first and second light beams is largely varied, and therefore the Lissajous figure L1$b$ has a substantial width in the direction of the ordinate. Namely, the fact that the Lissajous figure on the coordinate plane P1 has a substantial width in the direction of the ordinate suggests the existence of an artifact of the living body 20.

Such a Lissajous figure on the coordinate plane P1 can be displayed on a displaying section which is not shown. As compared with a simple display of a temporal variation of the intensity or the intensity ratio such as shown in the left half in FIG. 6, the user can more intuitively recognize an existence of an artifact.

As indicated by the broken line in FIG. 5, the medical photometer 10 can execute a process of reducing an artifact component from an acquired signal (step S36) when an instruction stored in the memory 62 is executed by the processor 61.

Figure 7A:
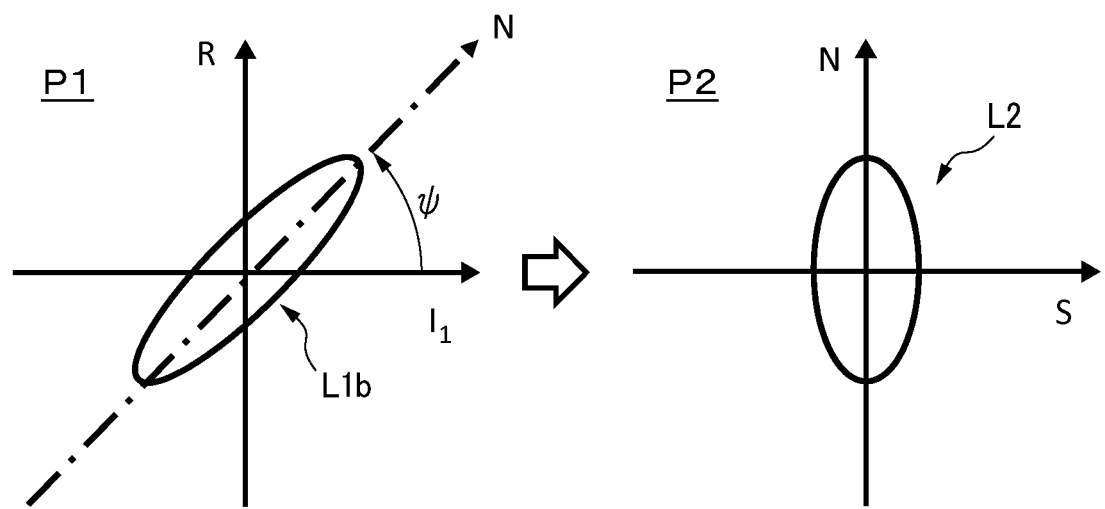
FIGS. 7A and 7B illustrate the operation of the medical photometer in FIG. 5.

As shown in FIG. 7A, specifically, a coordinate transformation from the coordinate plane P1 to a coordinate plane P2 is performed. The abscissa of the coordinate plane P2 indicates a component (signal component) S which is a component of an acquired intensity signal (in the example, the first intensity signal), and to which the pulsation of the living body 20 contributes. The ordinate of the coordinate plane P2 indicates a component (noise component) N which is a component of the acquired intensity signal, and to which an artifact of the living body 20 contributes.

The Lissajous figure L1$b$ which is formed in accordance with the artifact has a substantial width in both the directions of the abscissa and the ordinate. Therefore, the Lissajous figure L1$b$ has a slope $\Psi$ to the abscissa on the coordinate plane P1. In other words, the slope $\Psi$ is an angle between the abscissa and the N axis corresponding to the noise component of the Lissajous figure L1$b$.

The coordinate transformation is performed so as to make the direction of the slope $\Psi$ to coincide with the ordinate of the coordinate plane P2. As a result, a Lissajous figure L2 is obtained on the coordinate plane P2. In the Lissajous figure L2, the pulsation-contributed component and artifact-contributed component in the acquired first intensity signal are clearly separated from each other. When only the projection of the Lissajous figure L2 to the abscissa is extracted, therefore, the artifact-contributed component can be reduced from the first intensity signal, and only the pulsation-contributed component can be extracted.

As shown in FIG. 6, the actual Lissajous figure L1$b$ does not exhibit a simple shape such as shown in FIG. 7A. Therefore, the slope $\Psi$ in the coordinate plane P1 is determined by searching the value in the range from 0 to $\pi/2$, and by specifying a value at which the norm in the S-axis direction in the coordinate plane P2 is minimum.

The intensity of the second intensity signal is selected as the abscissa of the coordinate plane, and similar processes are performed, whereby only the pulsation-contributed component of the acquired second intensity signal can be extracted.

Figure 7B:
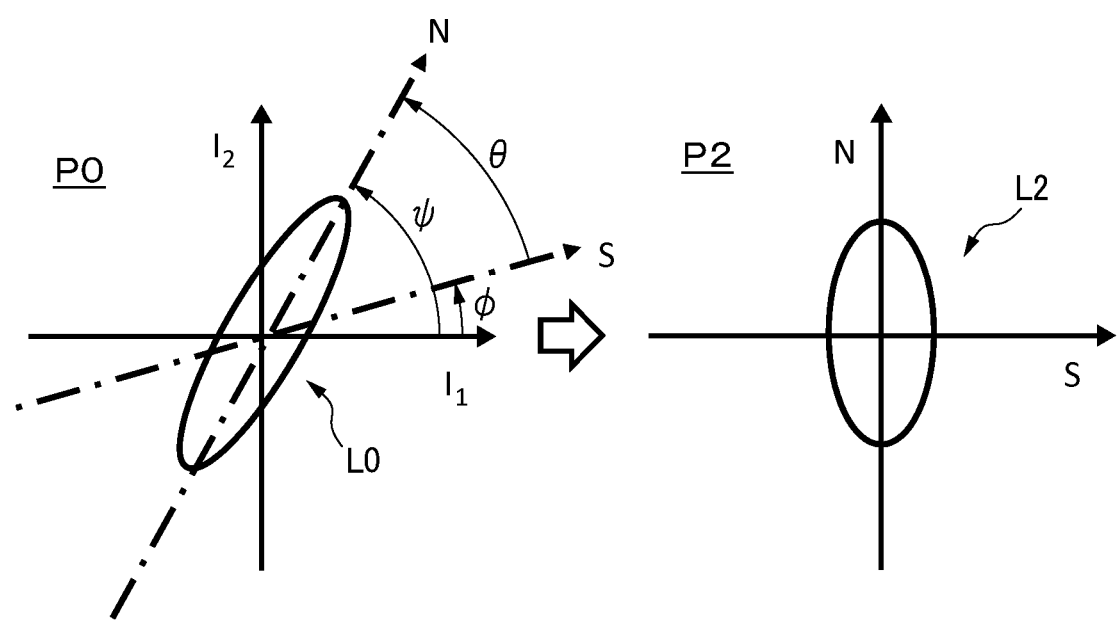

FIG. 7B diagrammatically illustrates a reduction method of an artifact component in a conventional pulse oximeter, as a comparative example. A coordinate plane P0 is used in the technique. The abscissa of the coordinate plane P0 corresponds to the variation rate of the intensity of a first light beam detected by a detector. The ordinate of the coordinate plane P0 corresponds to the variation rate of the intensity of a second light beam detected by the detector. The first and second light beams in this method are used for calculating the blood light absorber concentration, and different from those in the embodiments for calculating the amount of a weak light absorber in body.

A Lissajous figure L0 is formed in the thus configured coordinate plane P0. As seen from the figure, an S axis corresponding to the pulsation-contributed component (signal component), and an N axis corresponding to the artifact-contributed component (noise component) can be defined in the Lissajous figure L0. In order to finally obtain the Lissajous figure L2 on the coordinate plane P2 which is formed by the S and N orthogonal axes, therefore, it is required to consider both the coordinate transformation in which the S axis in the coordinate plane P0 is made to coincident with the abscissa in the coordinate plane P2, and that in which the N axis in the coordinate plane P0 is made to coincident with the ordinate in the coordinate plane P2.

In order to make the S axis in the coordinate plane P0 coincident with the abscissa in the coordinate plane P2, an angle $\phi$ between the S axis and the abscissa in the coordinate plane P0 must be specified. In the specification of the angle $\phi$, information of the blood light absorber concentration is required both because the blood light absorber concentration is indicated as a function of the extinction ratio of the first and second light beams and because the extinction ratio is indicated as a function of the angle $\phi$.

In order to make the N axis in the coordinate plane P0 coincident with the ordinate in the coordinate plane P2, an angle $\theta$ between the S axis and the N axis in the coordinate plane P0 must be specified. An angle $\Psi$ between the N axis and the abscissa in the coordinate plane P0 is determined by searching the value of $\theta$ in the range from $-\phi$ to $(\pi/2-\phi)$, and by specifying a value at which the norm in the S-axis direction in the coordinate plane P2 is minimum. An angle $\phi$ is obtained by subtract $\theta$ from angle $\Psi$.

The coordinate transformation from the coordinate plane P0 to the coordinate plane P2 is performed with the thus specified values of $\phi$ and $\theta$. The transformation technique is described in detail in Patent Literature 1, and therefore more detailed description is omitted here.

According to the technique of the embodiment shown in FIG. 7A, it is not necessary to previously acquire the blood light absorber concentration in order to perform the coordinate transformation, and it is requested to consider only the coordinate transformation of the N axis corresponding to the noise component in the Lissajous figure L1b. Therefore, an influence of an artifact can be reduced by a simpler configuration and with a lower control load.

As indicated by the broken line in FIG. 1, the medical photometer 10 of the embodiment may include the notifying section 17. The notifying section 17 is configured so as to perform notification when the degree of the detected artifact exceeds a predetermined value. The notification is performed by at least one of visual notification and auditory notification.

Specifically, the medical photometer 10 is configured so as to perform the processes indicated by the broken line in FIG. 5 when an instruction stored in the memory 62 is executed by the processor 61.

When an artifact is detected in step S34, it is determined whether the degree of the artifact exceeds the predetermined value or not (step S37). The predetermined value is adequately adjustable by the user. Specifically, it is determined whether the width in the direction along the ordinate of the Lissajous figure L1b shown in FIG. 6 exceeds the predetermined value or not. A situation where the conditions are continued to be satisfied for a predetermined period of time may be added to criteria for the determination.

If it is determined that the degree of the detected artifact exceeds the predetermined value (YES in step S37), the notification is performed (step S38). As described above, the notification can be performed by at least one of visual notification and auditory notification. After the notification, the process is transferred to step S35, and the above-described processes are repeated.

If it is determined that the degree of the detected artifact is equal to or smaller than the predetermined value (NO in step S37), the process is transferred to step S36, and the above-described processes are repeated.

According to the configuration, the user is notified of an artifact of the living body 20 which may disturb the operation of the medical photometer 10, and thereby the user can take adequate procedures. When the predetermined value is properly set, it is possible to notify of only a situation where procedures must be truly taken. This can prevent the working efficiency of the user from being lowered.

As described in the first embodiment, the first light emitter 11, the second light emitter 12, and the detector 14 can be integrated into a conventional pulse photometry probe including the third light emitter 13.

In conventional pulse photometry, in order to avoid a situation where an artifact has an adverse influence on a calculated result of the arterial oxygen saturation, an independent sensor (such as an acceleration sensor) for detecting an artifact must be attached to the living body. In the embodiment, by contrast, a configuration for calculating the tissue thickness can be integrated into a probe for calculating the arterial oxygen saturation, and moreover an artifact can be detected with the probe. Therefore, a situation where an artifact has an adverse influence on a calculated result of the arterial oxygen saturation can be avoided without adding an independent sensor.

The above-described embodiments are mere examples for facilitating understanding of the presently disclosed subject matter. The configurations of the embodiments may be adequately changed or improved without departing from the spirit of the presently disclosed subject matter. It is obvious that equivalents are included within the technical scope of the presently disclosed subject matter.

In the above-described embodiments, both the first light beam emitted from the first light emitter 11, and the second light beam emitted from the second light emitter 12 are infrared light beams. However, a configuration where both the first and second light beams are red light beams may be employed. In this case, conditions are that the extinction of the weak light absorber in body at the first wavelength $\lambda_1$ of the first light beam, and that of the weak light absorber in body at the second wavelength $\lambda_2$ of the second light beam are substantially different from each other, and that a material which is higher in extinction than the weak light absorber in body has substantially equal extinctions at the first wavelength $\lambda_1$ and the second wavelength $\lambda_2$. In the case of water and hemoglobin shown in FIG. 3, light beams of 700 nm and 730 nm may be selected as the first and second light beams.

In the above-described embodiments, the arterial oxygen saturation is used as an example of the blood light absorber concentration. However, the presently disclosed subject matter can be applied also to a configuration for calculating the concentration of another blood light absorber. Examples of another blood light absorber are carboxyhemoglobin, methemoglobin, and a dye injected into blood vessels. In this case, the wavelengths of the light beams are selected so that a ratio of the extinction coefficient of blood at these wavelengths is varied depending on the concentration of the target light absorber contained in the blood.

In the third embodiment which has been described with reference to FIGS. 6 and 7, the variation rate (I1 or I2) of the intensity of the first or second intensity signal is selected as the abscissa of the coordinate plane P1, and the variation rate (R) of the intensity ratio of the first and second intensity signals is selected as the ordinate. In the coordinate plane P2 which is obtained by the coordinate transformation from the coordinate plane P1, the abscissa indicates the signal component (S), and the ordinate indicates the noise component (N). However, the variation rate (I1 or I2) of the intensity of the first or second intensity signal may be selected as the ordinate of the coordinate plane P1, and the variation rate (R) of the intensity ratio of the first and second intensity signals may be selected as the abscissa. In this case, in the coordinate plane P2 after the coordinate transformation, the ordinate indicates the signal component (S), and the abscissa indicates the noise component (N).

What is claimed is:

1. A medical photometer comprising:
a first light emitter that emits a first light beam having a first wavelength;
a second light emitter that emits a second light beam having a second wavelength;
a detector that outputs a first intensity signal corresponding to an intensity of the first light beam that is transmitted through or reflected from a tissue of a living body, and a second intensity signal corresponding to an intensity of the second light beam that is transmitted through or reflected from the tissue;
a processor; and
a memory that stores an instruction readable by a computer,
wherein, when the instruction is executed by the processor, the medical photometer acquires a first light attenuation of the first light beam based on the first intensity signal, acquires a second light attenuation of the second light beam based on the second intensity signal, calculates a tissue thickness of the tissue of the living body based on a ratio of the first light attenuation and the second light attenuation, detects a temporal variation of an intensity ratio of the first intensity signal and the second intensity signal, cancels a temporal variation of the intensity ratio corresponding to pulsation of blood in the living body from the temporal variation of the intensity ratio, detects an artifact in the temporal variation of the intensity ratio corresponding to a temporal variation of the tissue thickness of the tissue of the living body, and calculates at least one of arterial oxygen saturation, a fraction of carboxyhemoglobin, a fraction of methemoglobin, and a concentration of total hemoglobin based on the artifact, both the first light beam and the second light beam are infrared light beams or red light beams, a ratio of a first extinction coefficient of a first blood light absorber at the first wavelength and a second extinction coefficient of the first blood light absorber at the second wavelength is different from 1, a third extinction coefficient of a second blood light absorber at the first wavelength is higher than the first extinction coefficient, a fourth extinction coefficient of the second blood light absorber at the second wavelength is higher than the second extinction coefficient, and a ratio of the third extinction coefficient and the fourth extinction coefficient is approximable by 1.

2. The medical photometer according to claim 1 further comprising a notifying section that performs notification when the detected artifact exceeds a threshold value.

3. The medical photometer according to claim 1 further comprising a third light emitter that emits a third light beam having a third wavelength,
wherein a ratio of an extinction coefficient of blood at the first wavelength and an extinction coefficient of the blood at the third wavelength is varied in accordance with a concentration of the second blood light absorber contained in the blood,
a ratio of an extinction coefficient of blood at the second wavelength and the extinction coefficient of the blood at the third wavelength is varied in accordance with a concentration of the second blood light absorber contained in the blood,
the detector outputs a third intensity signal corresponding to an intensity of the third light beam which is transmitted through or reflected from the tissue, and,
when the instruction is executed by the processor, the medical photometer acquires a light attenuation variation of the first light beam due to the pulsation of the blood in the living body, based on the first intensity signal and/or a light attenuation variation of the second light beam due to the pulsation, based on the second intensity signal, acquires a light attenuation variation of the third light beam due to the pulsation of the blood in the living body, based on the third intensity signal, calculates the concentration of the second blood light absorber in the blood based on the light attenuation variation of the third light beam and at least one of the light attenuation variation of the first light beam and the light attenuation variation of the second light beam, and calculates the at least one of arterial oxygen saturation, a fraction of carboxyhemoglobin, a fraction of methemoglobin, and a concentration of total hemoglobin based on the concentration of the second blood light absorber in the blood.

4. A medical photometer comprising:
a processor; and
a memory that stores an instruction readable by a computer,
wherein, when the instruction is executed by the processor, the medical photometer acquires from a probe a first light attenuation of a first light beam that has a first wavelength and that is transmitted through or reflected from a tissue of a living body, based on a first intensity signal corresponding to an intensity of the first light beam, acquires from the probe a second light attenuation of a second light beam that has a second wavelength and that is transmitted through or reflected from the tissue of the living body, based on a second intensity signal corresponding to an intensity of the second light beam, calculates a tissue thickness of the tissue of the living body based on a ratio of the first light attenuation and the second light attenuation, detects a temporal variation of an intensity ratio of the first intensity signal and the second intensity signal, cancels a temporal variation of the intensity ratio corresponding to pulsation of blood in the living body from the temporal variation of the intensity ratio, detects an artifact in a temporal variation of an intensity ratio of the first intensity signal and the second intensity signal corresponding to a temporal variation of the tissue thickness of the tissue of the living body, and calculates at least one of arterial oxygen saturation, a fraction of carboxyhemoglobin, a fraction of methemoglobin, and a concentration of total hemoglobin based on the artifact, a ratio of a first extinction coefficient of a first blood light absorber at the first wavelength and a second extinction coefficient of the first blood light absorber at the second wavelength is different from 1, a third extinction coefficient of a second blood light absorber at the first wavelength is higher than the first extinction coefficient, a fourth extinction coefficient of the second blood light absorber at the second wavelength is higher than the second extinction coefficient, and a ratio of the third extinction coefficient and the fourth extinction coefficient is approximable by 1.

5. A method of controlling a medical photometer comprising:

causing the medical photometer to acquire from a probe a first light attenuation of a first light beam that has a first wavelength and is transmitted through or reflected from a tissue of a living body, based on a first intensity signal corresponding to an intensity of the first light beam;

causing the medical photometer to acquire from the probe a second light attenuation of a second light beam that has a second wavelength and is transmitted through or reflected from the tissue, based on a second intensity signal corresponding to an intensity of the second light beam;

causing the medical photometer to calculate a tissue thickness of the tissue of the living body based on a ratio of the first light attenuation and the second light attenuation;

causing the medical photometer to detect a temporal variation of an intensity ratio of the first intensity signal and the second intensity signal and cancel a temporal variation of the intensity ratio corresponding to pulsation of blood in the living body from the temporal variation of the intensity ratio;

causing the medical photometer to detect an artifact in a temporal variation of an intensity ratio of the first intensity signal and the second intensity signal corresponding to a temporal variation of the tissue thickness of the tissue of the living body; and causing the medical photometer to calculate at least one of arterial oxygen saturation, a fraction of carboxyhemoglobin, a fraction of methemoglobin, and a concentration of total hemoglobin based on the artifact, wherein a ratio of a first extinction coefficient of a first blood light absorber at the first wavelength and a second extinction coefficient of the first blood light absorber at the second wavelength is different from 1, a third extinction coefficient of a second blood light absorber at the first wavelength is higher than the first extinction coefficient, a fourth extinction coefficient of the second blood light absorber at the second wavelength is higher than the second extinction coefficient, and a ratio of the third extinction coefficient and the fourth extinction coefficient is approximable by 1.

\* \* \* \* \*